(12) United States Patent
Spataro

(10) Patent No.: US 11,819,656 B2
(45) Date of Patent: Nov. 21, 2023

(54) EXTENSION TUBE CLAMP PROVIDING POSITIVE DISPLACEMENT

(71) Applicant: Becton, Dickinson and Company, Franklin Lakes, NJ (US)

(72) Inventor: Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/730,308

(22) Filed: Apr. 27, 2022

(65) Prior Publication Data

US 2022/0249828 A1   Aug. 11, 2022

Related U.S. Application Data

(63) Continuation of application No. 16/793,948, filed on Feb. 18, 2020, now Pat. No. 11,351,354.

(60) Provisional application No. 62/808,119, filed on Feb. 20, 2019.

(51) Int. Cl.
*A61M 39/28* (2006.01)
*A61M 39/08* (2006.01)
*A61M 39/10* (2006.01)

(52) U.S. Cl.
CPC ............ *A61M 39/28* (2013.01); *A61M 39/08* (2013.01); *A61M 39/10* (2013.01); *A61M 2039/1077* (2013.01)

(58) Field of Classification Search
CPC ................ A61M 39/28; A61M 39/281; A61M 39/283–288; A61M 1/7413; A61M 1/7415; A61M 1/743; A61M 39/08; A61M 39/10; A61M 2039/1077
See application file for complete search history.

(56) References Cited

U.S. PATENT DOCUMENTS

| | | | |
|---|---|---|---|
| 2,471,623 A * | 5/1949 | Hubbell | A61M 39/28 604/185 |
| 5,246,426 A | 9/1993 | Lewis et al. | |
| 6,929,235 B1 * | 8/2005 | Height | A61M 39/285 137/553 |
| 2007/0049999 A1 | 3/2007 | Esch et al. | |

(Continued)

FOREIGN PATENT DOCUMENTS

| | | |
|---|---|---|
| CN | 105209109 A | 12/2015 |
| CN | 109069802 A | 12/2018 |

(Continued)

*Primary Examiner* — Kevin C Sirmons
*Assistant Examiner* — Leah J Swanson
(74) *Attorney, Agent, or Firm* — Kirton McConkie; Whitney Blair; Kevin Stinger

(57) ABSTRACT

An extension set may include a clamp, which may include a housing and an actuator. The actuator may be movable between a raised position and a depressed position with respect to the housing. The actuator may include a bump profile. The extension set may include an extension tube, which may be disposed within the housing. The extension tube may include a loop. In response to movement of the actuator between the raised position and the depressed position with respect to the housing, the bump profile may progressively clamp the extension tube along the loop. The loop may facilitate an increased fluid volume flowing distally towards a catheter in response to actuating the clamp.

20 Claims, 8 Drawing Sheets

(56) References Cited

U.S. PATENT DOCUMENTS

| | | |
|---|---|---|
| 2007/0191775 A1 | 8/2007 | Diep et al. |
| 2008/0097330 A1 | 4/2008 | King et al. |
| 2009/0254034 A1 | 10/2009 | Beck et al. |
| 2010/0168682 A1 | 7/2010 | Braga |
| 2012/0083737 A1 | 4/2012 | Beck |
| 2012/0296275 A1 | 11/2012 | Martin |
| 2013/0324975 A1 | 12/2013 | Douglas et al. |
| 2015/0223977 A1 | 4/2015 | Oberkircher et al. |
| 2016/0089180 A1 | 3/2016 | Entabi |
| 2017/0296798 A1 | 10/2017 | Kume |
| 2019/0008551 A1 | 1/2019 | Entabi |
| 2019/0388653 A1 | 12/2019 | Breindel et al. |

FOREIGN PATENT DOCUMENTS

| | | |
|---|---|---|
| DE | 102016112598 | 1/2018 |
| DE | 102016112598 A1 | 1/2018 |
| EP | 0307743 | 3/1989 |
| WO | 2008/011258 | 1/2008 |
| WO | 2008011258 A1 | 1/2008 |
| WO | 2011/073766 | 6/2011 |
| WO | 2013/137348 | 9/2013 |
| WO | 2013137348 A1 | 9/2013 |
| WO | 2014/169428 | 10/2014 |
| WO | 2015/062101 | 5/2015 |

* cited by examiner

EXTENSION TUBE CLAMP PROVIDING POSITIVE DISPLACEMENT

RELATED APPLICATIONS

This application is a continuation of U.S. patent application Ser. No. 16/793,948, filed on Feb. 18, 2020, and entitled EXTENSION TUBE CLAMP PROVIDING POSITIVE DISPLACEMENT, which claims the benefit of United States Provisional Application No. 62/808,119, filed on Feb. 20, 2019, and entitled EXTENSION TUBE CLAMP PROVIDING POSITIVE DISPLACEMENT, which are incorporated herein in their entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral IV catheter ("PIVC"). As its name implies, the over-the-needle PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the PIVC in place for future blood withdrawal and/or fluid infusion.

A needleless connector may be used to connect the PIVC with a medical device for fluid administration or blood withdrawal. The medical device may include a transfusion bag, syringe, or the like. Currently, many needleless connectors reflux, meaning they draw blood and fluid from the vasculature into the catheter upon disconnection of the medical device from the needleless connector. This connector-driven reflux is not desirable due to the increased potential for reduced PIVC dwell times, which may result from clotting and occlusion within the PIVC. Systems and methods described in the present disclosure can mitigate and/or overcome these drawbacks.

The subject matter claimed herein is not limited to embodiments that solve any disadvantages or that operate only in environments such as those described above. Rather, this background is only provided to illustrate one example technology area where some implementations described herein may be practiced.

SUMMARY

In some embodiments, an extension set may include a clamp, which may include a housing and an actuator. In some embodiments, the actuator may be movable between a raised position and a depressed position with respect to the housing. In some embodiments, the actuator may include a bump profile. In some embodiments, the extension set may include an extension tube, which may be disposed within the housing. In some embodiments, the extension tube may include a loop.

In some embodiments, in response to movement of the actuator between the raised position and the depressed position with respect to the housing, the bump profile may progressively clamp the extension tube along the loop. In some embodiments, the loop may facilitate an increased fluid volume flowing distally towards a catheter in response to movement of the actuator to the depressed position.

In some embodiments, in response to movement of the actuator between the raised position and the depressed position with respect to the housing, the bump profile may contact a distal portion of the loop prior to contacting a proximal portion of the loop. In some embodiments, the bump profile may be configured to force fluid disposed within the loop distally in response to movement of the actuator from the raised position to the depressed position.

In some embodiments, the housing may include one or more protrusions. In some embodiments, the actuator may include one or more grooves. In some embodiments, the protrusions may be disposed within the grooves to orient the actuator within the housing. In some embodiments, the protrusions and the grooves may prevent the actuator from rotating with respect to the housing.

In some embodiments, the actuator may include a head, which may be disposed outside the housing. In some embodiments, the head may contact an outer surface of the housing in response to movement of the actuator to the depressed position. In some embodiments, the head of the actuator may be disposed proximate a body of the actuator. In some embodiments, a diameter of the head may be greater than a diameter of the body. In some embodiments, the body may include the bump profile.

In some embodiments, the housing may include a distal opening and a proximal opening. In some embodiments, the extension tube may extend through the distal opening and the proximal opening. In some embodiments, the loop may be disposed between the distal opening and the proximal opening. In some embodiments, an interior of the housing may include one or more support elements, which may be configured to contact the extension tube to support the extension tube and maintain the loop in a loop configuration.

In some embodiments, the extension set may include a needleless connector coupled to the extension tube. In some embodiments, a catheter system may include the extension set and a catheter assembly. In some embodiments, the catheter assembly may include a catheter adapter and a catheter extending distally from the catheter adapter. In some embodiments, the extension tube may be coupled to the catheter adapter.

In some embodiments, a method of clamping the extension tube may include placing a first digit of a hand of a user on the actuator. In some embodiments, the first digit of the hand of the user may include a thumb. In some embodiments, the method may include placing a second digit and a third digit of the hand of the user on a side of the housing opposite the actuator and the first digit. In some embodiments, the method may include depressing the actuator with the first digit to move the actuator to the depressed position. In some embodiments, in response to depression of the actuator with the first digit, the bump profile may progressively clamp the extension tube along the loop.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
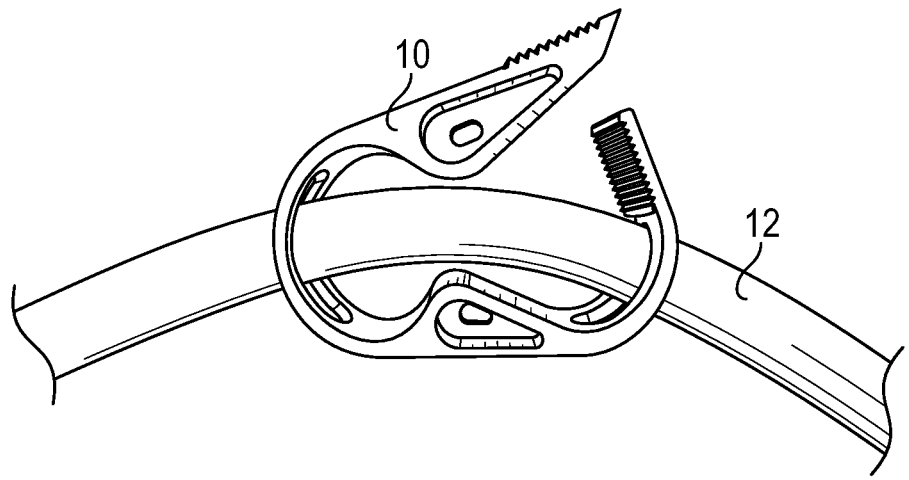
FIG. 1A is a side view of a prior art clamp, illustrating the prior art clamp in an unactuated position, according to some embodiments.
Figure 1B:
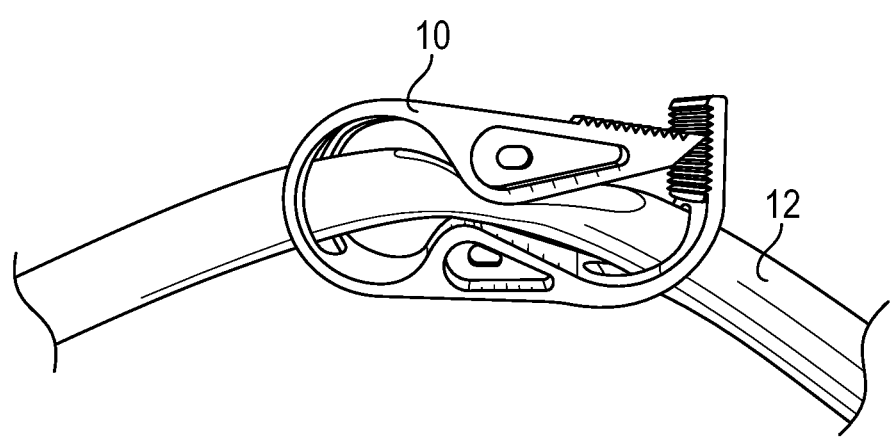
FIG. 1B is another side view of the prior art clamp of FIG. 1A, illustrating the prior art clamp in an actuated position, according to some embodiments.

Referring now to FIGS. 1A-1B, a prior art clamp 10 is illustrated. An extension tube 12 may extend from a PIVC (not illustrated in FIGS. 1A-1B) and through the prior art clamp 10. The extension tube 12 may be connected and proximal to the PIVC. The prior art clamp 10 attempts to overcome connector-driven reflux by distally displacing fluid along a given length of the extension tube 12 during clamping of the extension tube 12. In further detail, in response to the clinician actuating the prior art clamp 10, the prior art clamp 10 acts to squeeze fluid out of the extension tube 12 in the vicinity of the prior art clamp 10, resulting in some clamp-driven positive displacement or net positive output of fluid from the PIVC. However, the clamp-driven positive displacement may be relatively small.

Figure 2:
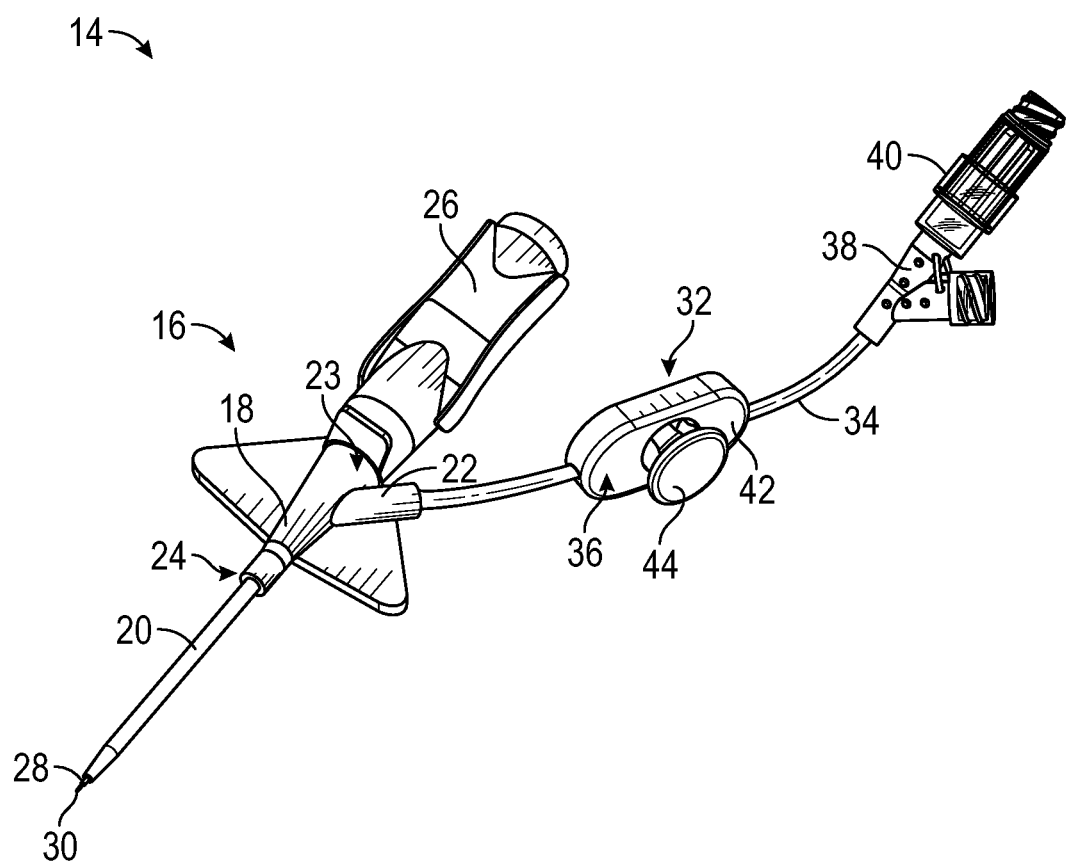
FIG. 2 is an upper perspective view of an example catheter system, according to some embodiments.

Referring now to FIG. 2, an example catheter system 14 is illustrated, according to some embodiments. In some embodiments, the catheter system 14 may include a catheter assembly 16. In some embodiments, the catheter assembly 16 may include a catheter adapter 18 and a catheter 20 extending distally from the catheter adapter 18. In some embodiments, the catheter adapter 18 may include a side port 22 in fluid communication with the lumen of the catheter adapter 18. In some embodiments, the catheter adapter 18 may include a proximal end 23, a distal end 24, and a lumen extending there between. In some embodiments, the catheter 20 may include a PIVC.

In some embodiments, the catheter assembly 16 may be removably coupled to a needle assembly, which may include a needle hub 26 and an introducer needle 28. In some embodiments, the introducer needle 28 may include a sharp distal tip 30. In some embodiments, a proximal end of the introducer needle 28 may be secured within the needle hub 26. In some embodiments, the introducer needle 28 may extend through the catheter 20 when the catheter assembly 16 is in an insertion position ready for insertion into vasculature of a patient, as illustrated, for example, in FIG. 2. In some embodiments, in response to the introducer needle 28 being inserted into the vasculature of the patient, flashback of blood may flow through the sharp distal tip 30 of the introducer needle 28 and may be visible to a clinician between the introducer needle 28 and the catheter 20 and/or at another location within the catheter assembly 16.

In some embodiments, in response to confirmation via the blood flashback that the catheter 20 is positioned within vasculature of the patient, the needle assembly may be removed from the catheter assembly 16. In some embodiments, when the needle assembly is coupled to the catheter assembly 16, as illustrated, for example, in FIG. 2, the introducer needle 28 of the needle assembly may extend through a septum disposed within the lumen of the catheter adapter 18.

In some embodiments, the catheter system 14 may include an extension set 32, which may include an extension tube 34 and a clamp 36. In some embodiments, a distal end of the extension tube 34 may be integrated with the catheter adapter 18, as illustrated, for example, in FIG. 2. For example, the extension tube 34 may be integrated with the side port 24 of the catheter adapter 18. In some embodiments, the extension tube 34 may be removably coupled to the catheter adapter 18, as illustrated, for example, in FIG. 7. In some embodiments, the clamp 36 may selectively close off the extension tube 34 to prevent blood or another fluid from flowing through the extension tube 34.

In some embodiments, the extension set 32 may include an adapter 38 coupled to a proximal end of the extension tube 34. In some embodiments, the adapter 38 may include a Y-adapter or another suitable connector. In some embodiments, a needleless connector 40 may be coupled to the adapter 38. In some embodiments, the adapter 38 and/or the needleless connector 40 may be used to connect the catheter 20 with a medical device for fluid administration or blood withdrawal. The medical device may include a transfusion bag, syringe, or any other suitable medical device. In some instances, the needleless connector 40 may reflux, meaning the needleless connector 40 may draw blood and fluid from the vasculature into the catheter 20 upon disconnection of the medical device from the needleless connector 40. This connector-driven reflux may not be desirable due to the increased potential for reduced catheter dwell times, which may result from clotting and occlusion within the catheter system 14.

In some embodiments, the clamp 36 may facilitate positive displacement or net positive output of fluid from the PIVC. In some embodiments, in response to actuation of the clamp 36, fluid may be pushed out of the clamp 36 and into the catheter assembly 16, which may be connected to the extension tube 34 and disposed distal to the clamp 36. The fluid that is pushed out of the clamp 36 may be pushed into the catheter 20 and into the patient.

In some embodiments, the clamp 36 may include a housing 42 and an actuator 44. In some embodiments, the housing 42 may be constructed of multiple pieces, which may be coupled together, or the housing 42 may be monolithically formed as a single unit. Similarly, in some embodiments, the actuator 44 may be constructed of multiple pieces, which may be coupled together, or the actuator 44 may be monolithically formed as a single unit. It is understood that the size, shape, and configuration of the housing 42 and/or the actuator 44 may vary.

Figure 3A:
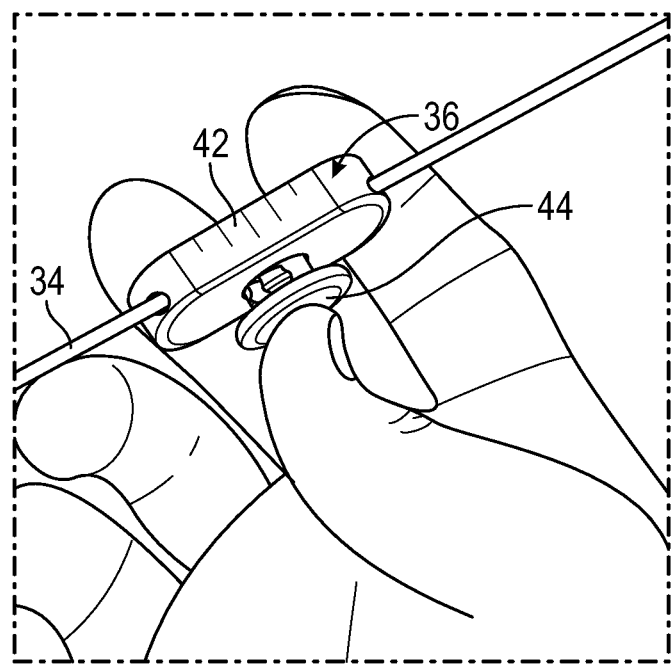
FIG. 3A is an upper perspective view of an example clamp of the catheter system of FIG. 2, illustrating an example actuator of the clamp in a raised position, according to some embodiments.
Figure 3B:
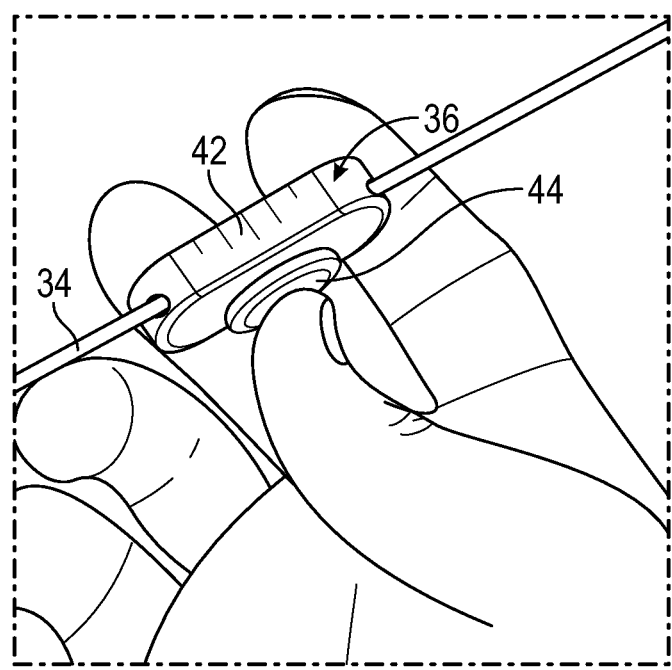
FIG. 3B is an upper perspective view of the clamp of FIG. 3A, illustrating the actuator in a depressed position, according to some embodiments.

Referring now to FIGS. 3A-3B, in some embodiments, the actuator 44 may be movable between a raised position and a depressed position with respect to the housing 42. The raised position is illustrated in FIG. 3A, according to some embodiments. The depressed position is illustrated in FIG. 3B, according to some embodiments. In some embodiments, the clinician may move the actuator 44 to the depressed position to actuate the clamp 36. In some embodiments, the actuator 44 may include a head 45, which may be disposed outside the housing 42. In some embodiments, the head 45 may contact an outer surface of the housing 42 when the actuator 44 is in the depressed position. In some embodiments, the head 45 may not contact the outer surface of the housing 42 when the actuator 44 is in the depressed position.

In some embodiments, a method of clamping the extension tube 34 may include placing a first digit of a hand of a user on the actuator 44, as illustrated, for example, in FIGS. 3A-3B. In some embodiments, the first digit of the hand of the user may include a thumb. In some embodiments, the method may include placing a second digit and a third digit of the hand of the user on a side of the housing 42 opposite the actuator 44 and the first digit as illustrated, for example, in FIGS. 3A-3B. In some embodiments, the method may include pinching the clamp to depress the actuator 44 and move the actuator 44 to the depressed position. In some embodiments, in response to depression of the actuator 44 with the first digit, the bump profile may progressively clamp the extension tube 34 along the loop.

Figure 4A:
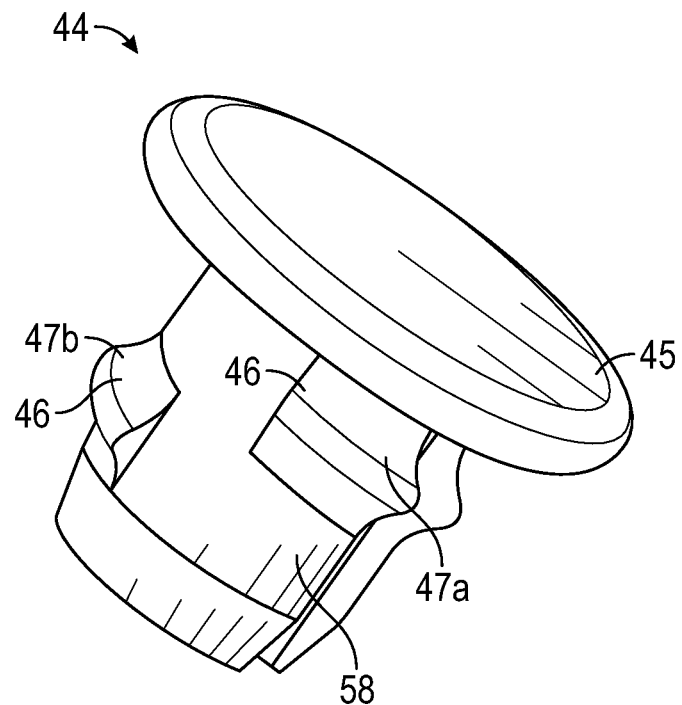
FIG. 4A is a side view of the actuator of the clamp of FIG. 3A, according to some embodiments.
Figure 4B:
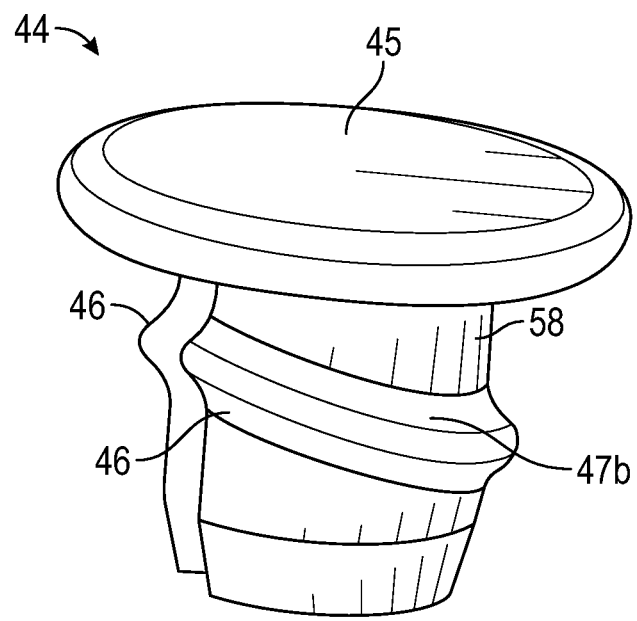
FIG. 4B is an opposite side view of the actuator of the clamp of FIG. 3A, according to some embodiments.

Referring now to FIGS. 4A-4B, in some embodiments, the actuator 44 may include a bump profile 46. In some embodiments, the head 45 of the actuator 44 may be disposed proximate a body 58 of the actuator 44. In some embodiments, a diameter of the head 45 may be greater than a diameter of the body 58. In some embodiments, the body 58 may include the bump profile 46. In some embodiments, the bump profile 46 may include one or more ridges 47. For example, the bump profile 46 may include a first ridge 47a and a second ridge 47b (which may be referred to in the present disclosure as "ridges 47"). In some embodiments, the one or more ridges 47 may form a spiral or corkscrew shape on the body 58. In some embodiments, the bump profile 46 may include one continuous ridge 47, which may form the spiral or corkscrew shape on the body 58.

In some embodiments, the spiral may include a curve that turns around an axis at a constant distance from the axis while moving parallel to the axis. In some embodiments, the curve may turn around the axis at a constant angle such that a pitch of the spiral, or the height of the spiral along one complete turn of the spiral, would be constant. In some embodiments, the curve may turn around the axis at a variable angle such that the pitch of the spiral would be variable. In some embodiments, the curve of the spiral may be mathematically optimized based on characteristics of a loop of the extension tube 34, such as a pitch of the loop.

Figure 5A:
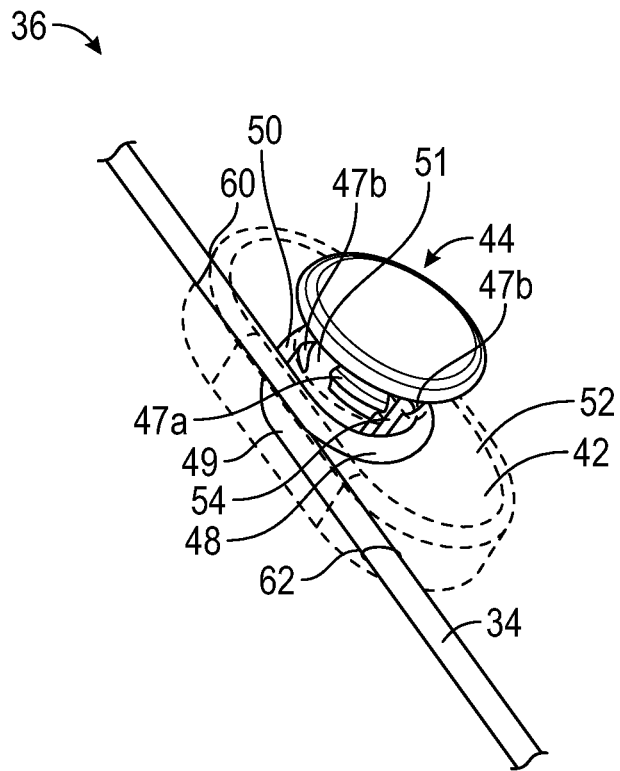
FIG. 5A is an enlarged view of the clamp of FIG. 3A, illustrating the actuator in the raised position, according to some embodiments.
Figure 5B:
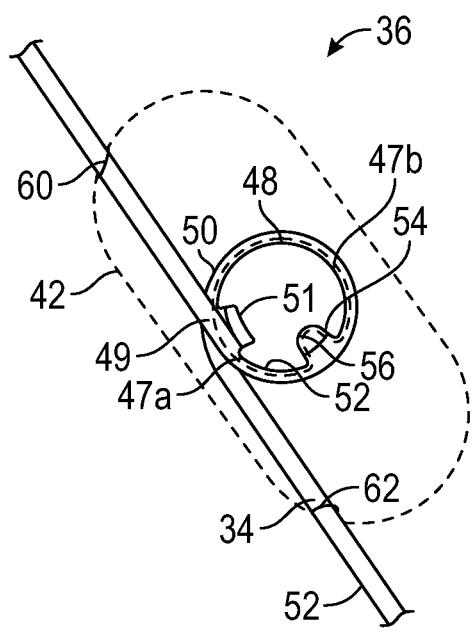
FIG. 5B is a top view of the clamp of FIG. 3A, illustrating the actuator in the depressed position and an example head of the actuator removed for illustration purposes, according to some embodiments.

Referring now to FIG. 5A-5C, in some embodiments, the extension tube 34 of the extension set 32 may include the loop 48. In some embodiments, in response to movement of the actuator 44 between the raised position and the depressed position with respect to the housing 42, the bump profile 46 may progressively clamp the extension tube 34 along the loop 48. In some embodiments, the loop 48 may facilitate an increased fluid volume flowing distally from the clamp 36 towards the catheter 20 in response to actuating the clamp 36.

In some embodiments, in response to movement of the actuator 44 between the raised position and the depressed position with respect to the housing 42, the bump profile 46 may contact a distal portion 50 of the loop 48 prior to contacting a proximal portion 52 of the loop 48. In some embodiments, an overlap portion 49 of the loop 48 may be disposed between the distal portion 50 and the proximal portion 52. In some embodiments, the bump profile 46 may be configured to force fluid disposed within the loop 48 distally in response to movement of the actuator 44 from the raised position to the depressed position. In some embodiments, the first ridge 47a may be spaced apart from the second ridge 47b to form a gap 51 that may be aligned with the overlap portion 49.

In some embodiments, the housing 42 may include one or more protrusions 54. In some embodiments, the actuator 44 may include one or more grooves 56. In some embodiments, the protrusions 54 may be disposed within the grooves 56 to orient the actuator 44 within the housing 42. In some embodiments, the protrusions 54 and the grooves 56 may prevent the actuator 44 from rotating with respect to the housing 42. In some embodiments, the housing 42 may not include the protrusions 54 and/or the actuator 44 may not include the grooves 56. In these and other embodiments, the first ridge 47a and the second ridge 47b may be connected or continuous.

In some embodiments, the housing 42 may include a distal opening 60 and/or a proximal opening 62. In some embodiments, the extension tube 34 may extend through the distal opening 60 and/or the proximal opening 62. In some embodiments, the loop 48 may be disposed between the distal opening 60 and the proximal opening 62.

Referring now to FIGS. 6A-6D, in some embodiments, an interior of the housing 42 may include one or more support elements 64, which may be configured to contact the extension tube 34 to support the extension tube 34 and maintain the loop 48 in a loop configuration. In some embodiments, the support elements 64 may include grooves and/or protrusions.

Figure 6A:
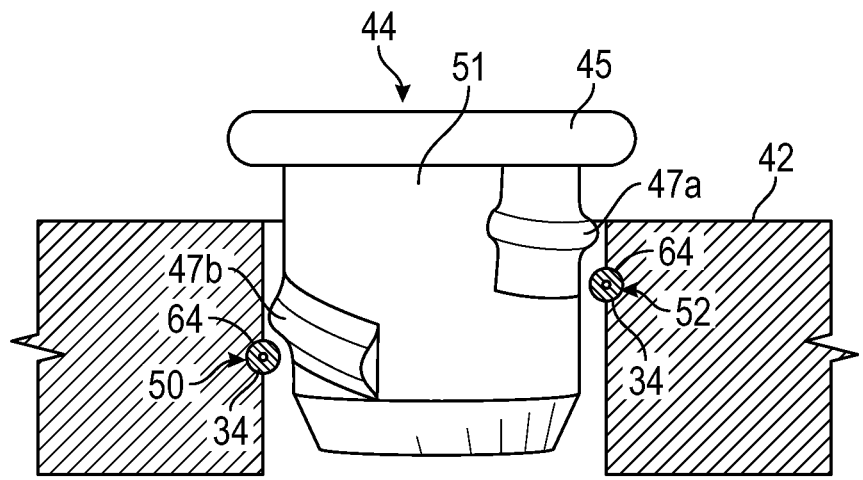
FIG. 6A is a partial cutaway view of the clamp of FIG. 3A, illustrating the actuator in the raised position, according to some embodiments.

FIG. 6A is a partial cutaway view of the clamp 36, illustrating the actuator 44 in the raised position, according to some embodiments. In some embodiments, when the actuator 44 is in the raised position, the one or more ridges 47 may not contact and/or pinch the extension tube 34. In some embodiments, when the actuator 44 is in the raised position, the one or more ridges 47 may not contact and/or clamp the loop 48. In some embodiments, when the actuator 44 is in the raised position, the one or more ridges 47 may not contact and/or clamp the distal portion 50 and the proximal portion 52. In some embodiments, in response to a portion of the extension tube 34 being clamped or pinched, fluid may be prevented from flowing through the portion.

Figure 6B:
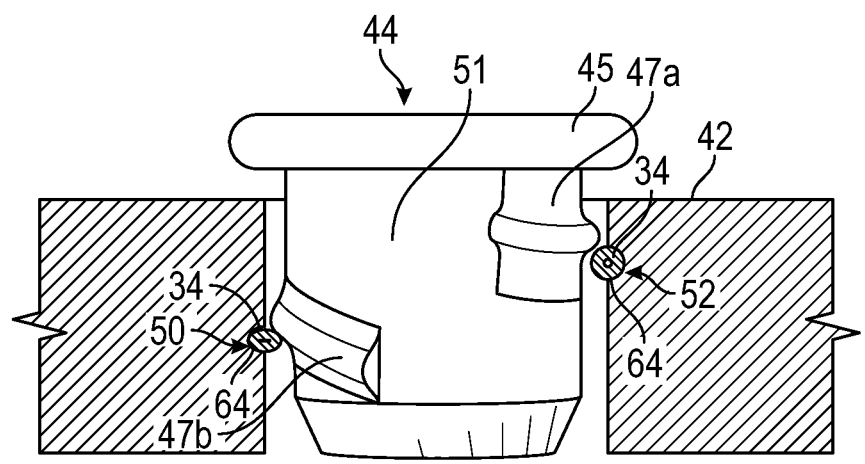
FIG. 6B is another partial cutaway view of the clamp of FIG. 3A, illustrating the clamp in a partially depressed position, according to some embodiments.
Figure 6C:
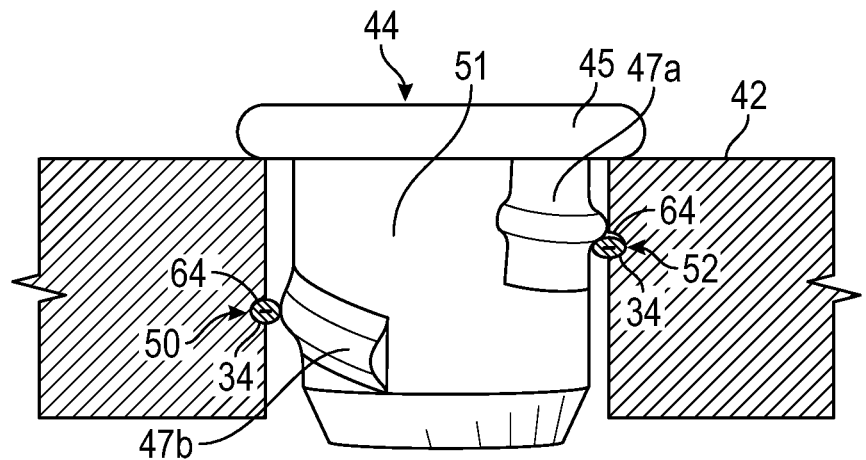
FIG. 6C is another partial cutaway view of the clamp of FIG. 3A, illustrating the clamp in the depressed position, according to some embodiments.

FIG. 6B is another partial cutaway view of the clamp 36, illustrating the clamp 36 in a partially depressed position, according to some embodiments. In some embodiments, when the actuator 44 is in the raised position, one or more of the ridges 47 may clamp the distal portion 50 but not the proximal portion 52. FIG. 6C is another partial cutaway view of the clamp 36, illustrating the clamp in the depressed position, according to some embodiments. In some embodiments, when the clamp 36 is in the depressed position, both the distal portion 50 and the proximal portion 52 may be clamped by the one or more ridges 47. Thus, FIGS. 6A-6C illustrate how the bump profile 46 may progressively clamp the extension tube 34 along the loop 48, according to some embodiments.

Figure 6D:
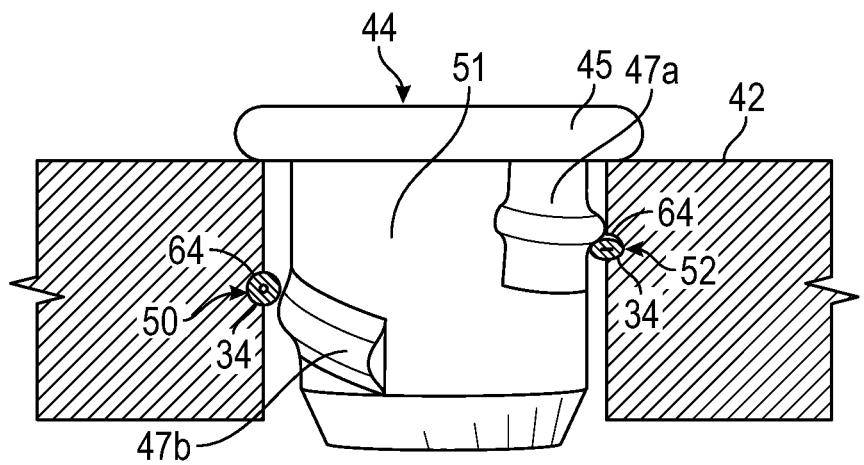
FIG. 6D is another partial cutaway view of the clamp of FIG. 3A, illustrating the clamp in the depressed position, according to some embodiments.

Referring now to FIG. 6D, another partial cutaway view of the clamp 36 in the depressed position is illustrated, according to some embodiments. In some embodiments, in response to the actuator 44 moving from the raised position to the depressed position, an area of contact between the ridges 47 and the extension tube 34 may rotate around a circumference of the actuator 44. In these embodiments, in response to the actuator 44 moving from the raised position to the depressed position, the area of contact between the ridges 47 and the extension tube 34 may not increase in size, which may reduce an input force necessary to close the clamp 36.

In these and other embodiments, as illustrated in FIG. 6D, in response to the actuator 44 moving from the raised position to the depressed position, a portion of the one or more ridges 47, such as a portion of the second ridge 47b, may move past the distal portion 50 and no longer contact and/or clamp the distal portion 50. In some embodiments, a portion of the one or more ridges 47 in contact with the extension tube 34 may move past the extension tube 34 to no longer contact and/or clamp the extension tube 34 in response to movement of the actuator 44 from the raised position to the depressed position. In some embodiments, the one or more ridges 47 may form the spiral to progressively clamp and/or move past the extension tube 34.

Figure 7:
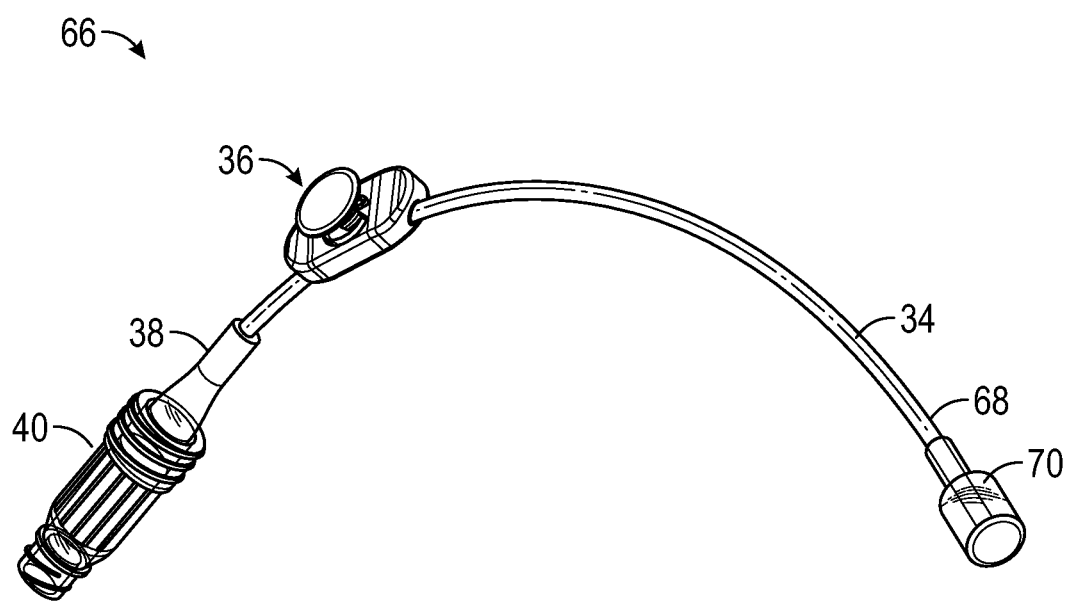
FIG. 7 is an upper perspective view of an example extension set that includes the clamp of FIG. 3A, according to some embodiments.

FIG. 7 is an upper perspective view of an example extension set 66 that includes the clamp 36, according to some embodiments. In some embodiments, a distal end 68 of the extension tube 34 may be coupled to the side port 22 (illustrated, for example, in FIG. 2) via a connector 70. In some embodiments, the connector 70 may include a luer adapter, such as, for example, a slip or thread male or female luer adapter. In some embodiments, the connector 70 may include a non-luer adapter. In some embodiments, the distal end 68 of the extension tube 34 may be integrated with the connector 70.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An extension set, comprising:
   a clamp, comprising:
      a housing; and
      an actuator movable between a raised position and a depressed position with respect to a longitudinal axis of the housing, wherein the actuator comprises a bump profile; and
   an extension tube disposed within the housing and looped around the actuator to form a loop, wherein in response to movement of the actuator between the raised position and the depressed position with respect to the housing, the bump profile progressively clamps the extension tube along the loop.

2. The extension set of claim 1, wherein the bump profile is configured to force fluid disposed within the loop distally in response to movement of the actuator from the raised position to the depressed position.

3. The extension set of claim 1, wherein in response to movement of the actuator between the raised position and the depressed position with respect to the housing, the bump profile contacts a distal portion of the loop prior to contacting a proximal portion of the loop.

4. The extension set of claim 1, wherein the housing comprises a protrusion, wherein the actuator comprises a groove, wherein the protrusion is disposed within the groove to orient the actuator within the housing.

5. The extension set of claim 1, wherein the actuator comprises a head disposed outside the housing, wherein the head contacts an outer surface of the housing in response to movement of the actuator to the depressed position.

6. The extension set of claim 5, wherein the head of the actuator is disposed proximate a body of the actuator, wherein a diameter of the head is greater than a diameter of the body, wherein the bump profile is disposed on the body.

7. The extension set of claim 1, wherein the housing comprises a distal opening and a proximal opening, wherein the extension tube extends through the distal opening and the proximal opening, wherein the loop is disposed within the housing between the distal opening and the proximal opening.

8. The extension set of claim 1, wherein an interior of the housing comprises a support element configured to contact the extension tube to support the extension tube and maintain the loop in a loop configuration.

9. The extension set of claim 1, further comprising a needleless connector coupled to the extension tube.

10. A catheter system, comprising:
    a catheter assembly, comprising:
       a catheter adapter; and
       a catheter extending distally from the catheter adapter;
    a clamp, comprising:
       a housing;
       an actuator movable between a raised position and a depressed position with respect to a longitudinal axis of the housing, wherein the actuator comprises a bump profile; and
    an extension tube coupled of the catheter adapter and looped around the actuator to form a loop, wherein in response to movement of the actuator between the raised position and the depressed position with respect to the housing, the bump profile progressively clamps the extension tube along the loop.

11. The catheter system of claim 10, wherein the bump profile is configured to force fluid disposed within the loop distally in response to movement of the actuator from the raised position to the depressed position.

12. The catheter system of claim 10, wherein in response to movement of the actuator between the raised position and the depressed position with respect to the housing, the bump profile contacts a distal portion of the loop prior to contacting a proximal portion of the loop.

13. The catheter system of claim 10, wherein the housing comprises a protrusion, wherein the actuator comprises a groove, wherein the protrusion is disposed within the groove to orient the actuator within the housing.

14. The catheter system of claim 10, wherein the actuator comprises a head disposed outside the housing, wherein the head contacts an outer surface of the housing in response to movement of the actuator to the depressed position.

15. The catheter system of claim 14, wherein the head of the actuator is disposed proximate a body of the actuator, wherein a diameter of the head is greater than a diameter of the body, wherein the bump profile is disposed on the body.

16. The catheter system of claim 10, wherein the housing comprises a distal opening and a proximal opening, wherein the extension tube extends through the distal opening and the proximal opening, wherein the loop is disposed within the housing between the distal opening and the proximal opening.

17. The catheter system of claim 10, wherein an interior of the housing comprises a support element configured to contact the extension tube to support the extension tube and maintain the loop in a loop configuration.

18. A method of clamping an extension tube, comprising:
placing a first digit of a hand of a user on an actuator of a clamp of an extension set, wherein the first digit includes a thumb, wherein the extension set comprises:
a clamp, comprising:
a housing; and
the actuator movable between a raised position and a depressed position with respect to a longitudinal axis of the housing, wherein the actuator comprises a bump profile;
an extension tube looped around the actuator to form a loop;
placing a third digit and a fourth digit of the hand of the user on a side of the housing opposite the actuator; and
depressing the actuator with the first digit to move the actuator to a depressed position with respect to the housing, wherein in response to depressing the actuator with the first digit, the bump profile progressively clamps the extension tube along the loop.

19. The method of claim 18, wherein the bump profile is configured to force fluid disposed within the loop distally in response to depression of the actuator.

20. The method of claim 18, wherein in response to movement of the actuator between the raised position and the depressed position with respect to the housing, the bump profile contacts a distal portion of the loop prior to contacting a proximal portion of the loop.

* * * * *